United States Patent [19]

Suzuki et al.

[11] Patent Number: 5,319,085
[45] Date of Patent: Jun. 7, 1994

[54] QUINOLINE DERIVATIVE HAVING SEROTONIN-3 RECEPTOR ANTAGONIZING ACTIVITY

[75] Inventors: Fumio Suzuki, Mishima; Hiroaki Hayashi, Tokyo; Yoshikazu Miwa, Sunto; Takeshi Kuroda, Ibaraki; Akio Ishii, Sunto; Shunji Ichikawa, Tagata; Ichiro Miki, Sunto; Katsuichi Shuto, Ube, all of Japan

[73] Assignee: Kyowa Hakko Kogyo Co., Ltd., Tokyo, Japan

[21] Appl. No.: 39,131

[22] PCT Filed: Dec. 25, 1991

[86] PCT No.: PCT/JP91/01758

§ 371 Date: Apr. 16, 1993

§ 102(e) Date: Apr. 16, 1993

[87] PCT Pub. No.: WO92/12150

PCT Pub. Date: Jul. 23, 1992

[30] Foreign Application Priority Data

Dec. 28, 1990 [JP] Japan .................... 2-409388

[51] Int. Cl.$^5$ ................ C07D 403/12; C07D 401/12
[52] U.S. Cl. ................................................. 546/126
[58] Field of Search ........................................ 546/126

[56] References Cited

U.S. PATENT DOCUMENTS 4,797,406 1/1989 Richardson et al. ............. 514/299

FOREIGN PATENT DOCUMENTS 0323077 7/1989 European Pat. Off. ............ 546/126

Primary Examiner—Alan L. Rotman
Attorney, Agent, or Firm—Fitzpatrick, Cella, Harper & Scinto

[57] ABSTRACT

Quinoline derivatives represented by formula (I):

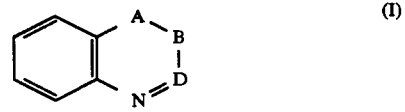

wherein A-B-D represents —C(COO—Y)=CH—C(OR)= (wherein Y represents 8-methyl-8-azabicyclo[3.2.1]oct-3-yl group and R represents alkyl) or —C(OH)=C(COX—Y)—CH= (wherein X represents —O— or —NH—; and Y has the same meaning as described above), or a pharmaceutically acceptable salt thereof, possess potent 5HT$_3$ antagonizing activity and are useful as antiemetic agents.

4 Claims, No Drawings

QUINOLINE DERIVATIVE HAVING SEROTONIN-3 RECEPTOR ANTAGONIZING ACTIVITY

TECHNICAL FIELD

The present invention relates to a quinoline derivative having a serotonin-3 receptor (hereafter referred to as $5HT_3$) antagonizing activity.

BACKGROUND ART

It is known that $5HT_3$ antagonists exhibit an antiemetic activity, an antianxious activity, a suppressing activity of mental disorders, etc. [Trends in Pharmacological Sciences, 8, 501 (1987)]. $5HT_3$ antagonists are effective against carcinostatic agent-induced vomiting, which has not been cured by dopamine antagonists. The $5HT_3$ antagonists are thus expected to be antiemetics of new type [Br. J. Cancer, 56, 159 (1987)].

It is disclosed in Japanese Published Unexamined Patent Application No. 72886/85 (U.S. Pat. No. 4,797,406) that quinoline derivatives represented by formula (A):

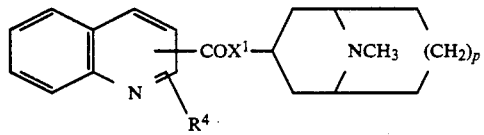

wherein $R^4$ represents hydrogen, hydroxy or a lower alkoxy ($C_1$ to $C_4$); $X^1$ represents —O— or —NH—; and p represents 0 or 1, have a $5HT_3$ antagonizing activity and an antiarrhythmic activity. That publication merely discloses a compound having azabicyclononane ring (p=1) in formula (A) (hereafter referred to as Compound C):

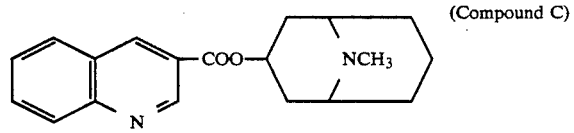

(Compound C)

but is silent about any specific compounds having azabicyclooctane ring (p=0). It is also disclosed in Japanese Published Unexamined Patent Application No. 41429/88 (GB-A-2193633) that the compounds represented by formula (A) are effective against vomiting caused by carcinostatic agents such as Cisplatin. Further, Japanese Published Unexamined Patent Application No. 203365/89 (EP-B-0323077) describes quinoline derivatives represented by formula (B):

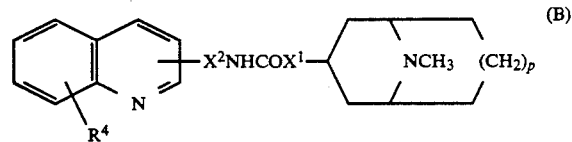

wherein $X^2$ represents a single bond or CO, and $R^4$, $X^1$ and p have the same meanings as described above, but no specific compounds having formula (B) are disclosed therein.

DISCLOSURE OF THE INVENTION

The present invention relates to quinoline derivatives represented by formula (I):

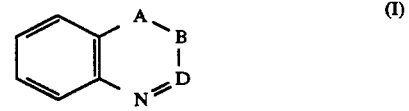

wherein A-B-D represents —C(COO—Y)=CH—C(OR)=[hereafter referred to as formula(α)](wherein Y represents 8-methyl-8-azabicyclo[3.2.1]oct-3-yl group and R represents methyl, ethyl, propyl, isopropyl, butyl, isobutyl, pentyl or hexyl) or —C(OH)=C(COX—Y)—CH=[hereafter referred to as formula (β)](wherein X represents —O— or —NH—; and Y has the same meaning as described above), or a pharmaceutically acceptable salt thereof.

Hereafter the compounds represented by formula (I) are referred to as Compound (I). With respect to the compounds of other formula numbering, the same shall apply.

As the pharmaceutically acceptable salt of Compound (I), mention may be made of inorganic acid salts such as hydrochlorides, sulfates, phosphates, etc.; organic acid salts such as acetates, maleates, fumarates, tartarates, citrates, etc.

The processes for preparing Compound (I) are described below.

In the following processes, where the defined group changes under conditions given or is inappropriate for practicing the processes, the group may be treated in a manner conventional to organic synthetic chemistry, for example, protection of a functional group, removal of the protection, etc. so that the processes may be easily carried out.

Process 1

Compound (Ia) which is Compound (I) where A-B-D means formula (α), may be obtained according to the following reaction equation in the presence of a base:

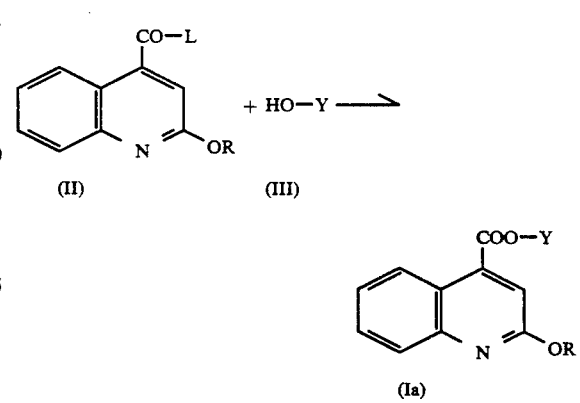

wherein R and Y have the same meanings as described above and L represents a leaving group.

Herein, the leaving group denoted by L refers to halogen such as chlorine, bromine, iodine, etc.; alkoxy such as methoxy, ethoxy, etc.; aryloxy such as phenoxy, p-nitrophenoxy etc.; alkoxycarbonyl such as ethoxycarbonyl, isobutyloxycarbonyl, etc.; 1-imidazolyl group; 1-pyrrolidyl group, etc.

Compound (II) can be prepared by the method of Reference Examples as described hereafter, or according to a similar manner thereto. Compound (II) is commercially available, as the case may be. Compound (III) is a known compound which can be prepared by the method as described in Japanese Published Unexamined Patent Application No. 28085/82.

As the reaction solvent, any solvent may be used singly or in combination, so long as it is inert to the reaction. Mention may be made of ethers such as tetrahydrofuran, dioxane, etc.; dimethylamides such as dimethylformamide, dimethylacetamide, etc.; ketones such as acetone, methyl ethyl ketone, etc.; alcohols such as methanol, ethanol, isopropyl alcohol, etc.; halogenated hydrocarbons such as methylene chloride, chloroform, dichloroethane, etc.; esters such as ethyl acetate, etc.; and dimethylsulfoxide, etc. As the base used in the reaction, mention may be made of alkali metal bicarbonates such as sodium bicarbonate, potassium bicarbonate, etc.; alkali metal carbonates such as sodium carbonate, potassium carbonate, etc.; alkali metal hydrides such as sodium hydride, etc.; alkali metal alkoxides such as sodium methoxide, sodium ethoxide, etc.; alkali metal salts such as n-butyl lithium, etc.

The reaction is carried out at $-30°$ to $150°$ C., preferably at $-10°$ to $100°$ C. and generally completed in 30 minutes to 20 hours.

Process 2

Compound (Ib) which is Compound (I) where A-B-D means formula ($\beta$) may be obtained by hydrolyzing Compound (IV)

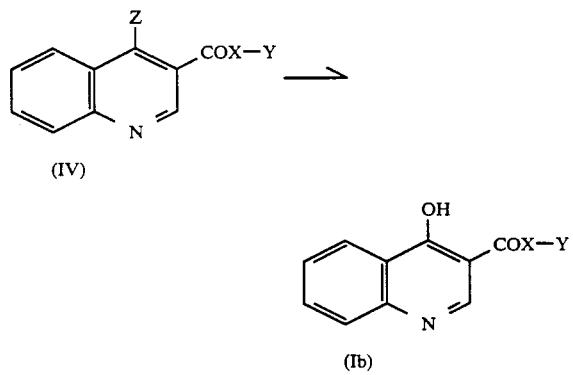

(IV)

(Ib)

wherein X and Y have the same meanings as described above and Z represents halogen such as chlorine, bromine and iodine in an acidic aqueous solution such as a hydrochloric acid aqueous solution, etc.

Compound (IV) may be prepared in a similar manner to Process 1. The reaction is carried out at 0° to 150° C., preferably at room temperature to 100° C. and completed generally in 30 minutes to 20 hours, though the reaction period varies depending upon the reaction temperature.

The intermediates and the desired products in the process described above may be isolated and purified by subjecting these compounds to purification means conventionally used in organic synthetic chemistry, for example, filtration, extraction, washing, drying, concentration, recrystallization, various chromatographies, etc. The intermediates may also be provided for the next reaction without particularly purifying them.

Where it is desired to obtain the salts of Compound (I), Compound (I) may be purified as it is in case that Compound (I) is obtained in a form of salt. In case that Compound (I) is obtained in a free form, the salts may be formed by dissolving or suspending Compound (I) in an appropriate solvent and adding an acid thereto to form a salt of Compound (I).

Compound (I) and its pharmaceutically acceptable salts may also be present in the form of addition products to water or various solvents. These addition products are also included in the present invention.

Structural formulae of specific compounds in the present invention obtained in the foregoing processes and Compound C are shown in Table 1. In the table, Compounds 8 and 9 are new compounds which are not covered by formula (A).

TABLE 1

| Compound No. | E | G | J |
|---|---|---|---|
| 1 | AZ1 | H | $-O(CH_2)_3CH_3$ |
| 2 | AZ1 | H | $-O(CH_2)_2CH_3$ |
| 3 | AZ1 | H | $-OCH(CH_3)_2$ |
| 4 | AZ1 | H | $-OCH_3$ |
| 5 | $-OH$ | AZ1 | H |
| 6 | $-OH$ | AZ2 | H |
| 7 | AZ1 | H | $-OCH_2CH(CH_3)_2$ |
| 8 | AZ1 | H | $-O(CH_2)_4CH_3$ |
| 9 | AZ1 | H | $-O(CH_2)_5CH_3$ |
| 10 | AZ1 | H | $-OC_2H_5$ |
| C | H | AZ3 | H |

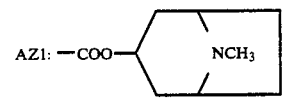

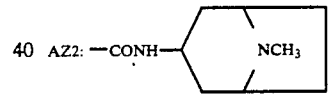

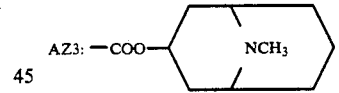

The pharmacological activities of Compound (I) are illustrated by referring to test examples.

TEST EXAMPLE 1

5HT$_3$ Receptor binding test

Using rat neuroblastoma-glyoma NG108-15 cell membrane fraction, the binding activities of the test compounds to 5HT$_3$ receptor were examined.

A membrane fraction of NG108-15 cells was prepared according to the method of Neijt et al. [Naunyn-Schmiedeberg's Arch. Parmacol. 337, 493–499 (1988)].

The receptor binding experiment was performed using [$^3$H] quipazine [J. Neurochem., 52, 1787 (1989)], a high affinity ligand to 5HT$_3$ receptor.

A membrane fraction obtained from $4\times10^5$ NG108-15 cells was suspended in 1 ml of 20 mM Tris-hydrochloride buffer (pH 7.5) containing 154 mM sodium chloride. Then, 2 nM [$^3$H] quipazine (2519.7 GBq/mmol; Du Pont Co., Ltd.) and various concentrations of the test compound were added to the suspension followed by incubating at 37° C. for 60 minutes.

Then, 4 ml of an ice-cooled buffer was added to terminate the reaction and then the mixture was filtered through CF/C glass fiber filter (Whatmann Co., Ltd.). The filter was washed with the buffer, and put in a scintillation vial. Scintisol EX-H (Wako Pure Chemicals, Inc.) was added to the scintillation vial. Radioactivity on the filter was counted in a liquid scintillation counter.

An inhibition rate of the [$^3$H] quipazine binding for the test compound was estimated according to the equation;

Inhibition rate (%) =

$$\left(1 - \frac{\text{binding in the presence} - \text{non-specific}}{\text{total binding}^* - \text{non-specific binding}^{**}}\right) \times 100$$

*"Total binding" is [$^3$H] quinpazine-binding in the abscence of test compound
**"Non-specific binding" is [$^3$H] quipazine-binding in the presence of 10 μM MDL72222
[Naunyn-Scmiedeberg's Arch. Pharmacol., 326, 36 (1984)].

Ki values were estimated based on the resultant inhibition rates according to the Cheng Prusoff equation.

In this test, the comparison was made between Compound (I) and Compound C disclosed in Japanese Published Unexamined Patent Application No. 72886/85 as the reference compound.

The results are shown in Table 2.

TABLE 2

| Compound | Inhibition Rate (%) (Concentration) | | Ki Value (nM) |
|---|---|---|---|
| | ($10^{-7}$M) | ($10^{-8}$M) | |
| 1Sa | 104 | 99 | 0.39 |
| 2Sa | 104 | 101 | 0.32 |
| 3Sa | 104 | 101 | 0.31 |
| 4Sa | 104 | 98 | 0.58 |
| 5S'a | 107 | — | 6.1 |
| 6Sa | 101 | 89 | 2.1 |
| 7Sa | 108 | 101 | 0.44 |
| 8Sa | 97 | 94 | 0.86 |
| 9Sa | 97 | 74 | 3.2 |
| 10Sa | 99 | 96 | 0.88 |
| CSa | 84 | 12 | 29 |

Sa and S'a mean the fumarate and the hydrochloride, of each compound, respectively.

Table 2 indicates that Compound (I) having azabicyclooctane ring has a lower Ki value and thus an excellent 5HT$_3$ antagonizing activity, as compared with Compound C having azabicyclononane ring.

TEST EXAMPLE 2

Activity against Cisplatin-induced vomiting

Female and male *Suncus mirinus* animals weighing 23 to 68 g were used, one group consisting of 5 to 10 animals. According to the method of Matsuki et al. (Japan J. Pharmacol., 48, 303 (1988)], the animals were isolated in metal mesh cage (one animal/one cage). One hour after, the test compound or physiological saline (control) was intraperitoneally administered (i.p.) in a volume of 10 ul/g of body weight. Further 30 minutes after administration of the test compound, Cisplatin (20 or 40 mg/kg) was intraperitoneally administered. After administration of Cisplatin, a time period (latency) for the first vomiting and the number of frequencies of vomiting caused in the period of 5 to 120 minutes after administration, were determined. The latency and the number of frequencies in the test compound administered group were compared with those in the control group. The test of significance was performed by Student's t-test.

The results in 40 mg/kg Cisplatin-administration model are shown in Table 3-1. The results in 20 mg/kg Cisplatin-administration model are shown in Table 3-2.

TABLE 3-1

| Compound | Number of Vomiting (mean ± S.E.M.) | Latency (min.) (mean ± S.E.M.) |
|---|---|---|
| Control | 28.0 ± 6.7 | 35.1 ± 4.4 |
| 5S'a Dose (mg/kg i.p.) | | |
| 0.1 | 29.6 ± 3.5 | 41.4 ± 0.7*** |
| 0.3 | 13.2 ± 4.8 | 69.6 ± 13.4* |
| 1.0 | 4.3 ± 2.4*** | 103.5 ± 10.3*** |
| 10.0 | 7.6 ± 7.6* | 105.1 ± 14.9** |

*p < 0.05
**p < 0.01
***p < 0.001
S'a means the hydrochloride of Compound 5.

TABLE 3-2

| Compound | Number of Vomiting (mean ± S.E.M.) | Latency (min.) (mean ± S.E.M.) |
|---|---|---|
| Control | 16.1 ± 2.1 | 46.5 ± 4.3 |
| 6Sa Dose (mg/kg i.p.) | | |
| 0.01 | 10.0 ± 4.0 | 58.2 ± 9.9 |
| 0.03 | 8.2 ± 1.4*** | 52.6 ± 4.2 |
| 0.1 | 7.4 ± 2.6*** | 85.7 ± 9.7* |
| 0.3 | 0.0 ± 0*** | 120.0 ± 0*** |
| 1.0 | 0.0 ± 0*** | 120.0 ± 0*** |

*p < 0.05
**p < 0.01
***p < 0.001
Sa means the hydrochlorode of Compound 6.

TEST EXAMPLE 3

Acute toxicity

The test Compound was orally and intraperitoneally administered to ddY strain male mice weighing 20 to 25 g. MLD (Minimum Lethal Dose) was determined by observing the mortality for 7 days after the administration.

The results are shown in Table 4.

TABLE 4

| Compound | MLD (mg/kg) | |
|---|---|---|
| | i.p. | p.o. |
| 1Sa | 200 | 100 |
| 2Sa | 100 | 100 |
| 3Sa | 200 | >100 |
| 4Sa | 200 | 50 |
| 5S'a | >300 | >100 |
| 6Sa | >300 | >100 |
| 7Sa | 300 | >100 |
| 8Sa | >300 | >100 |
| 9Sa | >300 | 50 |
| 10Sa | 100 | 50 |

Sa and S'a mean the fumarate and the hydrochloride, of each compound, respectively.

These results suggest that Compound (I) has an excellent 5HT$_3$ antagonizing activity and is useful for the treatment of nausea and vomiting which are side effects caused by chemotherapy and radiotherapy of cancer, and for the treatment of anxiety, mental disorders (for example, schizophrenia and mania), migraine, pain, etc.

Compound (I) or a pharmaceutically acceptable salt thereof may be used as it is or in various preparation forms. The pharmaceutical composition of the present invention can be prepared by uniformly mixing Compound (I) or a pharmaceutically acceptable salt thereof with pharmaceutically acceptable carriers. The pharmaceutical composition may be desirably in a single dose unit which is suited for oral or parenteral administration.

In preparing the composition in an oral administration form, any pharmaceutically acceptable carriers may be used. Liquid preparations for oral administration, for example, a suspension and a syrup, may be prepared using water; sugars such as sucrose, sorbitol, fructose, etc.; glycols such as polyethylene glycol, propylene glycol, etc.; oils such as sesami oil, olive oil, soybean oil, etc.; preservatives such as alkyl p-hydroxybenzoate, etc.; flavors such as strawberry flavor, peppermint, etc. Powders, pills, capsules and tablets may be prepared using excipients such as lactose, glucose, sucrose, mannitol, etc.; disintegrators such as starch, sodium alginate, etc.; lubricants such as magnesium stearate, talc, etc.; binders such as polyvinyl alcohol, hydroxypropyl cellulose, gelatin, etc.; surfactants such as fatty acid esters, etc.; plasticizers such as glycerine, etc. Tablets and capsules are the most useful single dose unit for oral administration since their administration is easy. When tablets or capsules are prepared, solid pharmaceutical carriers are used. Furthermore, a solution for parenteral administration may be prepared using carriers composed of distilled water, saline, a glucose solution or a mixture of saline and a glucose solution.

The effective dose of Compound (I) or its pharmaceutically acceptable salt and the number of administration may vary depending upon the form of administration, age, body weight, condition, etc. of a patient but it is generally preferred to administer in a dose of 0.01 to 25 mg/kg/day by dividing into 3 to 4 times.

Hereinafter the examples of the present invention and reference examples are given.

EXAMPLE 1

Endo-(8-methyl-8-azabicyclo[3.2.1]oct-3-yl) 2-n-butoxy-4-quinolinecarboxylate (Compound 1)

A mixture of 6.00 g (24.5 mmols) of Compound a obtained in Reference Example 1 and 50 ml of thionyl chloride was heated under reflux for 30 minutes. After concentration under reduced pressure, 90 ml of anhydrous tetrahydrofuran was added to the concentrate followed by stirring (Solution A).

A mixture of 3.73 g (26.4 mmols) of tropine and 18 ml of anhydrous tetrahydrofuran was stirred at 0° C. in an argon atmosphere and 16.4 ml (26.5 mmols) of 15% n-butyl lithiumhexane solution was added to the mixture. The mixture was stirred at 0° C. for further 15 minutes. After concentration under reduced pressure, 22 ml of anhydrous tetrahydrofuran and then Solution A were in sequence dropwise added to the concentrate in an argon atmosphere. The mixture was stirred at 0° C. for an hour. After concentration under reduced pressure, a small amount of methanol and water were added to the concentrate. After extracting with chloroform, the extract was dried over anhydrous sodium sulfate and the solvent wad distilled off under reduced pressure. The residue was purified by silica gel column chromatography (eluting solvent: chloroform/methanol=10/1) to give 2.73 g (yield 30%) of Compound 1.

While stirring at room temperature, 1.33 g (3.61 mmols) of Compound 1 and 0.42 g (3.62 mmols) of fumaric acid were dissolved in a mixture of 10 ml of isopropyl alcohol and a small amount of acetone. The solution was poured into hexane and the precipitated crystals were filtered and dried to give 1.28 g (yield 73%) of Compound 1 as the fumarate.

Melting point: 124.0° C.

MS (EI) m/e: 368 (M+)

IR (KBr) cm$^{-1}$: 3400 (br), 1723, 1603, 1216, 1026, 794

NMR (DMSO-d$_6$) δ(ppm): 8.49 (1H, d, J=8.4 Hz), 7.86 (1H, d, J=8.3 Hz), 7.74 (1H, m), 7.53 (1H, m), 7.39 (1H, s), 6.56 (2H, s), 5.29 (1H, m), 4.47 (2H, t, J=6.7 Hz), 3.60 (2H, m), 2.53 (3H, s), 1.9–2.5 (8H, m), 1.79 (2H, m), 1.48 (2H, m), 0.97 (3H, t, J=7.3 Hz)

EXAMPLE 2

Endo-(8-methyl-8-azabicyclo[3.2.1]oct-3-yl) 2-n-propoxy-4-quinolinecarboxylate (Compound 2)

Compound 2 was obtained as the fumarate (yield[1] 22%, yield[2] 69%) in a similar manner to Example 1, except for using Compound g obtained in Reference Example 3 in place of Compound a.

Hereafter yield[1] and yield[2] refer to a yield of the free form and a yield of the salt, respectively.

Melting point: 154.0°–162.0° C.

MS (EI) m/e: 354 (M+)

IR (KBr) cm$^{-1}$: 3430 (br), 1721, 1601, 1569, 1217, 1025, 792

NMR (DMSO-d$_6$) δ(ppm): 8.49 (1H, d, J=8.4 Hz), 7.86 (1H, d, J=8.3 Hz), 7.74 (1H, m), 7.53 (1H, m), 7.39 (1H, s), 6.55 (2H, s), 5.29 (1H, m), 4.42 (2H, t, J=6.8 Hz), 3.54 (2H, m), 2.49 (3H, s), 1.90–2.55 (8H, m), 1.83 (2H, m), 1.02 (3H, t, J=7.4 Hz)

EXAMPLE 3

Endo-(8-methyl-8-azabicyclo[3.2.1]oct-3-yl) 2-isopropoxy-4-quinolinecarboxylate (Compound 3)

Compound 3 was obtained as the fumarate (yield[1] 35%, yield[2] 87%) in a similar manner to Example 1, except for using Compound h obtained in Reference Example 4 in place of Compound a.

Melting point: 160.5°–161.0° C.

MS (EI) m/e: 354 (M+)

IR (KBr) cm$^{-1}$: 3440 (br), 1728, 1600, 1567, 1394, 1314, 1216, 1026, 795, 773

NMR (DMSO-d$_6$) δ(ppm): 8.49 (1H, d, J=8.4 Hz), 7.84 (1H, d, J=8.4 Hz), 7.73 (1H, m), 7.52 (1H, m), 7.33 (1H, s), 6.55 (2H, s), 5.52 (1H, m), 5.28 (1H, m), 3.54 (2H, m), 2.50 (3H, s), 1.85–2.55 (8H, m), 1.40 (6H, d, J=6.1 Hz)

EXAMPLE 4

Endo-(8-methyl-8-azabicyclo[3.2.1]oct-3-yl) 2-methoxy-4-quinolinecarboxylate (Compound 4)

Compound 4 was obtained as the fumarate (yield[1] 44%, yield[2] 77%) in a similar manner to Example 1, except for using Compound i obtained in Reference Example 5 in place of Compound a.

Melting point: 198.0°–200.5° C.

MS (EI) m/e: 326 (M+)

IR (KBr) cm$^{-1}$: 3440 (br), 1725, 1609, 1571, 1380, 1332, 1222, 1025, 794, 763

NMR (DMSO-d$_6$) δ(ppm): 8.52 (1H, d, J=8.4 Hz), 7.89 (1H, d, J=8.3 Hz), 7.76 (1H, m), 7.55 (1H, m), 7.41 (1H, s), 6.54 (2H, s), 5.29 (1H, m), 4.05 (3H, s), 3.51 (2H, m), 2.48 (3H, s), 1.85–2.55 (8H, m)

EXAMPLE 5

Endo-(8-methyl-8-azabicyclo[3.2.1]oct-3-yl) 4-hydroxy-3-quinolinecarboxylate (Compound 5)

A mixture of 1.32 g (7.00 mmols) of 4-hydroxy-3-quinolinecarboxylic acid and 15 ml of thionyl chloride was stirred at room temperature for 30 minutes. After concentration under reduced pressure, 30 ml of anhydrous tetrahydrofuran was added to the concentrate followed by stirring (Solution B).

A mixture of 1.68 g (11.90 mmols) of tropine and 5 ml of anhydrous tetrahydrofuran was stirred at 0° C. in an argon atmosphere and 7.4 ml (11.96 mmols) of 15% n-butyl lithiumhexane solution was added to the mixture. The mixture was stirred at 0° C. for further 15 minutes. After concentration under reduced pressure, 7 ml of anhydrous tetrahydrofuran and then Solution B were in sequence dropwise added to the concentrate in an argon atmosphere. The mixture was stirred at room temperature for 3 hours. After concentration under reduced pressure, the residue was subjected to column chromatography (eluting solvent: 20% methanol aqueous solution to 80% methanol aqueous solution) using DIAION SP207 (manufactured by Mitsubishi Chemical Industry Co., Ltd.). The obtained product was dissolved in a solvent mixture of chloroform and methanol and an ethyl acetate solution saturated with hydrogen chloride was further added to the solution. The solution was poured into cooled diethyl ether and the precipitated crystals were filtered and dried to give 0.56 g (yield 21%) of Compound 5 as the hydrochloride.

Melting point: 278°–280° C.

MS (EI) m/e: 312 (M+)

IR (KBr) cm$^{-1}$: 3420 (br), 1690, 1642, 1583, 1429, 1024, 767

NMR (DMSO-d$_6$) δ(ppm): 10.76 (1H, brs), 8.56 (1H, s), 8.20 (1H, d, J=7.7 Hz), 7.70 (2H, m), 7.42 (1H, m), 5.14 (1H, m), 3.86 (2H, m), 2.68 (3H, s), 1.8–2.9 (8H, m)

EXAMPLE 6

Endo-N-(8-methyl-8-azabicyclo[3.2.1]oct-3-yl)-4-hydroxy-3-quinolinecarboxamide (Compound 6)

A mixture of 0.68 g (2.06 mmols) of the free form of Compound n obtained in Reference Example 10 and 180 ml of 0.1N hydrochloric acid was stirred at 80° C. for 13 hours. After completion of the reaction, the reaction mixture was added to water. The mixture was washed with chloroform and a sodium bicarbonate aqueous solution was added to adjust pH to 7.5. The mixture was extracted with chloroform, and dried over anhydrous sodium sulfate. The solvent was distilled off under reduced pressure to give 0.64 g (yield 100%) of Compound 6.

0.24 g (2.07 mmols) of fumaric acid was added to 40 ml of an isopropyl alcohol solution containing 0.64 g of Compound 6, and the mixture was stirred at room temperature. To the mixture was added 15 ml of n-hexane at room temperature with stirring. The precipitated crystals were filtered and dried to give 0.64 g (yield 73%) of Compound 6 as the fumarate.

Melting point: 127.5°–128.9° C.

MS (EI) m/e: 311 (M+)

IR (KBr) cm$^{-1}$: 3400 (br), 1713, 1650, 1613, 1531, 1476, 1359, 759

NMR (DMSO-d$_6$) δ(ppm): 10.79 (1H, d, J=7.3 Hz), 8.75 (1H, s), 8.29 (1H, d, J=7.8 Hz), 7.69–7.75 (2H, m), 7.51 (1H, m), 6.55 (2H, s), 4.17 (1H, m), 3.73 (2H, m), 2.62 (3H, m), 1.80–2.55 (8H, m)

EXAMPLE 7

Endo-(8-methyl-8-azabicyclo[3.2.1]oct-3-yl) 2-isobutoxy-4-quinolinecarboxylate (Compound 7)

Compound 7 was obtained as the fumarate (yield[1] 22%, yield[2] 57%) in a manner similar to Example 1, except for using Compound j obtained in Reference Example 6 in place of Compound a.

Melting point: 162.0°–165.5° C.

MS (EI) m/e: 368 (M+)

IR (KBr) cm$^{-1}$: 3430 (br), 1726, 1601, 1568, 1383, 1326, 1219, 1026, 792, 769

NMR (DMSO-d$_6$) δ(ppm): 8.49 (1H, d, J=8.4 Hz), 7.86 (1H, d, J=8.4 Hz), 7.75 (1H, m), 7.54 (1H, m), 7.41 (1H, s), 6.56 (2H, s), 5.30 (1H, m), 4.25 (2H, d, J=6.6 Hz), 3.64 (2H, m), 2.56 (3H, s), 2.35–2.70 (2H, m), 1.90–2.30 (7H, m), 1.03 (6H, d, J=6.8 Hz)

EXAMPLE 8

Endo-(8-methyl-8-azabicyclo[3.2.1]oct-3-yl) 2-n-pentyloxy-4-quinolinecarboxylate (Compound 8)

Compound 8 was obtained as the fumarate (yield[1] 15%, yield[2] 53%) in a manner similar to Example 1, except for using Compound k obtained in Reference Example 7 in place of Compound a.

Melting point: 156.0°–160.0° C.

MS (EI) m/e: 382 (M+)

IR (KBr) cm$^{-1}$: 3420 (br), 1723, 1602, 1569, 1215, 1026, 973, 794, 770

NMR (DMSO-d$_6$) δ(ppm): 8.49 (1H, d, J=8.4 Hz), 7.85 (1H, d, J=8.3 Hz), 7.74 (1H, m), 7.53 (1H, m), 7.40 (1H, s), 6.56 (2H, s), 5.29 (1H, m), 4.46 (2H, t, J=6.7 Hz), 3.63 (2H, m), 2.55 (3H, s), 2.35–2.65 (2H, m), 1.95–2.30 (6H, m), 1.81 (2H, m), 1.25–1.55 (4H, m), 0.91 (3H, t, J=7.1 Hz)

EXAMPLE 9

Endo-(8-methyl-8-azabicyclo[3.2.1]oct-3-yl) 2-n-hexyloxy-4-quinolinecarboxylate (Compound 9)

Compound 9 was obtained as the fumarate (yield[1] 12%, yield[2] 59%) in a manner similar to Example 1, except for using Compound l obtained in Reference Example 8 in place of Compound a.

Melting point: 168.5°–169.0° C.

MS (EI) m/e: 396 (M+)

IR (KBr) cm$^{-1}$: 3430 (br), 1727, 1600, 1570, 1377, 1325, 1215, 1026, 795, 769

NMR (DMSO-d$_6$) δ(ppm): 8.49 (1H, d, J=8.5 Hz), 7.85 (1H, d, J=8.4 Hz), 7.74 (1H, m), 7.53 (1H, m), 7.39 (1H, s), 6.55 (2H, s), 5.28 (1H, m), 4.46 (2H, t, J=6.7 Hz), 3.53 (2H, m), 2.48 (3H, s), 2.30–2.65 (2H, m), 1.90–2.25 (6H, m), 1.80 (2H, m), 1.15–1.60 (6H, m), 0.88 (3H, t, J=6.9 Hz)

EXAMPLE 10

Endo-(8-methyl-8-azabicyclo[3.2.1]oct-3-yl) 2-ethoxy-4-quinolinecarboxylate (Compound 10)

Compound 10 was obtained as the fumarate (yield[1] 18%, yield[2] 90%) in a manner similar to Example 1, except for using Compound m obtained in Reference Example 9 in place of Compound a.

Melting point: 103.0°–103.5° C.

MS (EI) m/e: 340 (M+)

IR (KBr) cm$^{-1}$: 3420 (br), 1721, 1594, 1569, 1379, 1322, 1214, 1026, 790, 768

NMR (DMSO-d$_6$) δ(ppm): 8.50 (1H, d, J=8.4 Hz), 7.86 (1H, d, J=8.3 Hz), 7.75 (1H, m), 7.54 (1H, m), 7.39 (1H, s), 6.55 (2H, s), 5.28 (1H, m), 4.52 (2H, q, J=7.0 Hz), 3.54 (2H, m), 2.49 (3H, s), 2.30–2.60 (2H, m), 1.90–2.25 (6H, m), 1.41 (3H, t, J=7.0 Hz)

REFERENCE EXAMPLE 1

2-n-Butoxy-4-quinolinecarboxylic acid (Compound a)

While stirring at 0° C., 5.00 g (26.4 mmols) of 2-hydroxy-4-quinolinecarboxylic acid was added by small portions to 120 ml of a dimethylformamide solution containing 1.39 g (57.9 mmols) of sodium hydride. Under ice cooling, 70 ml of a dimethylformamide solution containing 10.7 g (58.0 mmols) of n-butyl iodide was dropwise added to the mixture with stirring. The mixture was stirred at room temperature for further one day. After completion of the reaction, a saturated sodium bicarbonate aqueous solution was added to the reaction mixture. The mixture was extracted with chloroform, and the extract was dried over anhydrous sodium sulfate. The solvent was distilled off under reduced pressure. The residue was purified by silica gel column chromatography (eluting solvent: hexane/ethyl acetate=7/1) to give 2.68 g (yield 34%) of 2-n-butoxy-4-n-butoxycarbonylquinoline (Compound b) from the first fraction.

NMR (CDCl$_3$) δ(ppm): 8.60 (1H, d, J=8.1 Hz), 7.88 (1H, d, J=8.1 Hz), 7.1–7.8 (3H, m), 4.2–4.8 (4H, m), 0.4–2.2 (14H, m)

A mixture of 2.67 g (8.86 mmols) of Compound b, 1.77 g of sodium hydroxide, 60 ml of water and 60 ml of dioxane was stirred at room temperature for an hour. The reaction mixture was concentrated under reduced pressure, and the residue was purified by silica gel column chromatography (eluting solvent: chloroform/methanol=5/1) to give 1.91 g (yield 90%) of Compound a.

NMR (DMSO-d$_6$) δ(ppm): 8.67 (1H, d, J=8.1 Hz), 6.95–7.85 (4H, m), 4.40 (2H, t, J=6.1 Hz), 1.10–1.95 (4H, m), 0.94 (3H, t, J=6.5 Hz)

REFERENCE EXAMPLE 2

Endo-(9-methyl-9-azabicyclo[3.3.1]non-3-yl) 3-quinolinecarboxylate (Compound C)

Compound C was prepared in a manner similar to the method described in Japanese Published Unexamined Patent Application No. 72886/85. Compound C was further converted into the fumarate in a manner similar to Example 2.

Melting point: 143.5°–144.0° C.

MS (EI) m/e: 310 (M+)

IR (KBr) cm$^{-1}$: 3380 (br), 1732, 1502, 1385, 1294, 1271, 1232, 1111, 981, 794, 770

REFERENCE EXAMPLE 3

2-n-Propoxy-4-quinolinecarboxylic acid (Compound g)

Compound g was obtained (yield[3] 38%, yield[4] 65%) in a manner similar to Reference Example 1, except for using n-propyl, iodide in place of n-butyl iodide.

Hereafter yield[3] and yield[4] refer to a yield of alkoxylation and esterification and a yield of hydrolysis of the ester, respectively.

REFERENCE EXAMPLE 4

2-Isopropoxy-4-quinolinecarboxylic acid (Compound h)

Compound h was obtained (yield[3] 86%, yield[4] 100%) in a manner similar to Reference Example 1, except for using isopropyl bromide in place of n-butyl iodide.

REFERENCE EXAMPLE 5

2-Methoxy-4-quinolinecarboxylic acid (Compound i)

Compound i was obtained (yield[3] 4%, yield[4] 100%) in a manner similar to Reference Example 1, except for using methyl iodide in place of n-butyl iodide.

REFERENCE EXAMPLE 6

2-Isobutoxy-4-quinolinecarboxylic acid (Compound j)

Compound j was obtained (yield[3] 16%, yield[4] 64%) in a manner similar to Reference Example 1, except for using isobutyl bromide in place of n-butyl iodide and changing the reaction conditions from at room temperature for one day to at 80° C. for 5 hours.

REFERENCE EXAMPLE 7

2-n-Pentyloxy-4-quinolinecarboxylic acid (Compound k)

Compound k was obtained (yield[3] 53%, yield[4] 100%) in a manner similar to Reference Example 1, except for using n-pentyl bromide in place of n-butyl iodide and changing the reaction conditions from at room temperature for one day to at 80° C. for 5 hours.

REFERENCE EXAMPLE 8

2-n-Hexyloxy-4-quinolinecarboxylic acid (Compound l)

Compound l was obtained (yield[3] 54%, yield[4] 99%) in a manner similar to Reference Example 1, except for using n-hexyl bromide in place of n-butyl iodide and changing the reaction conditions from at room temperature for one day to at 80° C. for 5 hours.

REFERENCE EXAMPLE 9

2-Ethoxy-4-quinolinecarboxylic acid (Compound m)

Compound m was obtained (yield[3] 26%, yield[4] 100%) in a manner similar to Reference Example 1, except for using ethyl iodide in place of n-butyl iodide.

REFERENCE EXAMPLE 10

Endo-(8-methyl-8-azabicyclo[3.2.1]-oct-3-yl)-4-chloro-3-quinolinecarboxamide (Compound n)

A mixture of 0.76 g (4.02 mmols) of 4-hydroxy-3-quinolinecarboxylic acid, 4 ml of thionyl chloride and a few drops of dimethylformamide was stirred at room temperature for 2 hours followed by concentration under reduced pressure (Solid C).

In an argon atmosphere, 30 ml of an anhydrous tetrahydrofuran solution containing 0.01 g (4.17 mmols) of sodium hydride was stirred at room temperature. 15 ml of an anhydrous tetrahydrofuran solution containing 0.56 g (3.99 mmols) of 3α-amino-8-methyl-8-azabicyclo[3.2.1]octane [J. Am. Chem. Soc., 79, 4194 (1957)] was added to the mixture. The resulting mixture was stirred at room temperature for further an hour. Solid C was gradually added to the resulting mixture followed by stirring at room temperature for 2 hours. After completion of the reaction, the reaction mixture was added to 1N hydrochloric acid, and the mixture was washed twice with chloroform. A saturated sodium bicarbonate aqueous solution was further added to the aqueous layer to render the layer weakly alkaline. The mixture was then extracted twice with chloroform. The chloroform layer was combined and dried over anhydrous sodium sulfate. The solvent was distilled off under reduced pressure and 25 ml of water was added to the residue followed by stirring. The precipitated crystals were filtered and dried to give 0.49 g (yield 37%) of Compound n.

0.49 g of Compound n was dissolved in methanol, and ethyl acetate saturated with hydrogen chloride was added to the solution. Ethyl acetate was further added to the solution. The precipitated crystals were filtered and dried to give 0.51 g (yield 85%) of Compound n as the hydrochloride.

Melting point: 181°–184° C.

MS (EI) m/e: 329 (M+)

IR (KBr) cm$^{-1}$: 1661, 1633, 1545, 1355

NMR (DMSO-d$_6$) δ(ppm): 10.80 (1H, d, J=6.8 Hz) 8.91 (1H, s), 8.33 (1H, d, J=8.3 Hz), 8.18 (1H, d, J=8.4 Hz), 7.97 (1H, m), 7.87 (1H, m), 4.06 (1H, m), 3.85 (2H, m), 2.66 (3H, s), 1.9–2.9 (8H, m)

We claim:

1. A compound of the formula

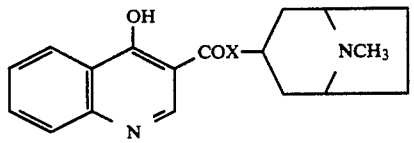

wherein (X) represents —O— or —NH—; or a pharmaceutically acceptable salt thereof.

2. A compound of the formula

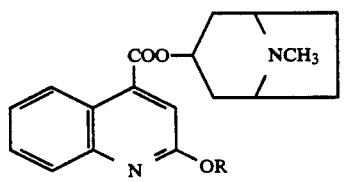

wherein (R) represents methyl, ethyl, propyl, isopropyl, butyl, isobutyl, pentyl or hexyl; or a pharmaceutically acceptable salt thereof.

3. Endo-(8-methyl-8-azabicyclo[3.2.1]oct-3-yl) 2-pentyloxy-4-quinolinecarboxylate or endo-(8-methyl-8-azabicyclo[3.2.1]oct-3-yl) 2-hexyloxy-4-quinolinecarboxylate, or a pharmaceutically acceptable salt thereof.

4. Endo-(8-methyl-8-azabicyclo[3.2.1]oct-3-yl) 2-butoxy-4-quinolinecarboxylate, endo-(8-methyl-8-azabicyclo[3.2.1]oct-3-yl) 2-propoxy-4-quinolinecarboxylate, endo-(8-methly-8-azabicyclo[3.2.1]oct-3yl) 2-isopropoxy-4-quinolinecarboxylate, endo-(8-methyl-8-azabicyclo[3.2.1]oct-3-yl) 2-methoxy-4-quinolinecarboxylate, endo-N-(8-methyl-8-azabicyclo[3.2.1]oct-3-yl) 4-hydroxy-3-quinolinecarboxylate, endo-(8-methyl-8-azabicyclo[3.2.1]oct-3-yl)-4-hydroxy-3-quinolinecarboxamide, endo-(8-methyl-8-azabicyclo[3.2.1]oct-3-yl) 2-isobutoxy-4-quinolinecarboxylate or endo-(8-methyl-8-azabicyclo[3.2.1]oct-3-yl) 2-ethoxy-4-quinolinecarboxylate, or a pharmaceutically acceptable salt thereof.

* * * * *